United States Patent
Loupas et al.

[11] Patent Number: 5,961,462
[45] Date of Patent: Oct. 5, 1999

[54] ULTRASONIC DOPPLER IMAGING AT HIGH FRAME RATES OF DISPLAY

[75] Inventors: Thanasis Loupas, Seattle; Charles Powrie, Duvall; Aline Laure Criton, Seattle, all of Wash.

[73] Assignee: ATL Ultrasound, Bothell, Wash.

[21] Appl. No.: 09/080,881

[22] Filed: May 18, 1998

[51] Int. Cl.[6] .................................................. A61B 8/02
[52] U.S. Cl. ........................................... 600/453; 600/455
[58] Field of Search .................................. 600/447, 453, 600/454, 455, 456, 457, 472

[56] References Cited

U.S. PATENT DOCUMENTS

| | | | |
|---|---|---|---|
| 4,217,909 | 8/1980 | Papadofrangakis et al. | 600/455 |
| 4,534,357 | 8/1985 | Powers | 600/472 |
| 5,313,947 | 5/1994 | Micco | 600/455 |
| 5,501,223 | 3/1996 | Washburn et al. | 600/455 |
| 5,685,308 | 11/1997 | Wright et al. | 600/447 |

*Primary Examiner*—Francis J. Jaworski
*Assistant Examiner*—Ali M. Imam
*Attorney, Agent, or Firm*—W. Brinton Yorks, Jr.

[57] ABSTRACT

The Doppler imaging of blood flow or slowly moving tissue at high frame rates of display is performed by oversampled acquisition of a Doppler ensemble from the body and display of Doppler information within a display range of Doppler values which is less than the range defined by said rate of oversampling. Preferably, Doppler information is acquired at the highest PRF for the depth of Doppler imaging. In one embodiment Doppler data is scaled in proportion to the ratio of the acquisition PRF to the display PRF. Alternatively, an embodiment of the present invention performs Doppler estimation by autocorrelation or spectral analysis which operates upon nonadjacent samples in the Doppler ensemble.

17 Claims, 4 Drawing Sheets

ULTRASONIC DOPPLER IMAGING AT HIGH FRAME RATES OF DISPLAY

This invention relates to ultrasonic diagnostic imaging systems and, in particular, to Doppler ultrasonic diagnostic imaging at high frame rates of display.

The ultrasonic pulse echo imaging of structures, whereby received echo signals are amplitude detected and arranged in an image in consideration of their time of flight, is commonly referred to as B mode imaging. B mode imaging can be done at relatively high frame rates of display, since only one transmit pulse is needed for each image line of the display. Following transmission of an ultrasonic beam in a given direction, a sequence of echoes is received from along the beam direction, from the near field to the far field. The time between transmit pulses is the time required to receive echoes from the greatest image depth in the beam direction. The time required to gather echoes for a complete image is approximately equal to (a) the total number of lines required to form the image multiplied by (b) the time between pulses. This means that all of the image lines for an image with a maximum depth of 10 cm can be acquired more quickly than a like number of lines of an image with a maximum depth of 20 cm. Consequently, the greater the depth of the image, the longer the time to acquire the image data and hence the slower the frame rate.

The frame rate of display for B mode imaging, variable as it may be, is still considerably faster than the frame rate of display for Doppler images such as power Doppler and colorflow images. This is because each Doppler image line must be interrogated a number of times in order to estimate the Doppler shift at points along the line. Each interrogation along the line acquires a full line of echo data, and the set of samples acquired over time for each point on the image line is referred to as an ensemble. The ensembles of data are needed to estimate the Doppler shift by fast Fourier transform or autocorrelation at each point along the line. The number of transmit pulses required to gather a full ensemble of samples reduces the frame rate of display below that required to acquire the same image frame for B mode display.

The frame rate of display can decline even further when the user is applying Doppler to image slow rates of bloodflow or tissue movement inside the body. This is because the ensemble transmit pulse rate, referred to as the pulse repetition frequency or PRF, must be dropped so as to adequately sample the slow motion of flow or movement. A number of techniques involving the time-multiplexed interleaving of ensemble acquisition along a number of image lines have been proposed to address this problem. While making better use of the available imaging time, these techniques have not been able to dramatically improve the frame rate of display for slow flow conditions. It would be desirable to augment these techniques with others which are able to detect slow flow conditions while maintaining a high frame rate of display.

In accordance with the principles of the present invention an ultrasonic Doppler system is provided in which the acquisition PRF may be operated at a higher rate than the display PRF. Preferably the acquisition PRF is operated at the highest rate for the chosen maximum Doppler display depth. The acquired Doppler data is then processed to estimate the Doppler phase shift or frequency in accordance with the desired display PRF, and the resultant Doppler display data is scaled for the appropriate display range. This technique allows high resolution Doppler frequency estimation and high frame rates of display even under low flow conditions.

Figure 1:
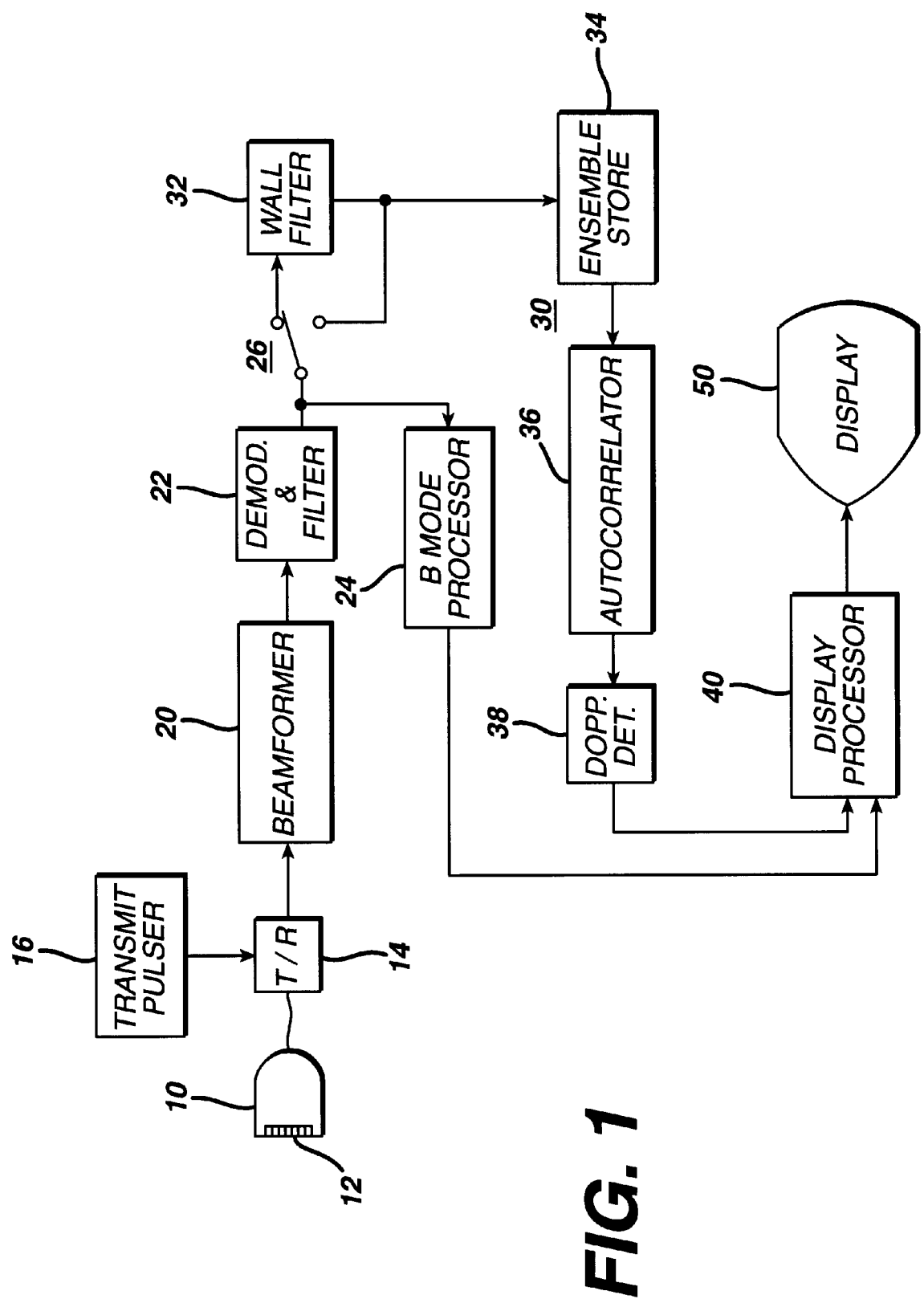
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. An ultrasonic probe 10 includes an array transducer 12 which transmits pulsed beams of ultrasonic waves into the body and receives echoes reflected back to the transducer from cells and tissues in the body. The transmission by the probe is controlled by a transmit pulser 16, connected to the probe by a transmit/receive (T/R) switch 14, which determines the waveform characteristics and times of transmission by elements of the transducer array necessary to transmit and focus the desired ultrasonic beam in a given direction. Following each pulsed transmission by the transducer array echoes are returned over time from increasing depths along the beam direction, referred to herein as a "line" of echo information. Each line of echoes is coupled by the T/R switch 14 to a beamformer 20, which delays and combines echo components from the individual elements of the array 12 to form a sequence of coherent echo information along the line. The coherent echo information is demodulated to a desired intermediate or base band of frequencies and filtered by a demodulator and filter circuit 22.

The lines of coherent echo data may then be directed along several paths for processing. One path directs the echoes to a B mode processor 24, where the echoes are amplitude detected and processed, then coupled to a display processor 40 for assembly and display of an ultrasonic B mode image on an image display 50. The B mode image will display the tissue structure in the region of the body being imaged, and may be displayed alone or in combination with Doppler information depicting motion in the imaged region. For Doppler display the lines of echo information may be applied to a wall filter which eliminates low frequency, large amplitude echo information from slow moving or stationary structures such as the walls of the heart or blood vessels. The remaining information is echo information from moving fluids such as bloodflow. An ensemble of lines of bloodflow information is Doppler processed by a Doppler processor 30 and coupled to the display processor 40 where the speed, intensity or other detected characteristic of bloodflow is color-coded and overlaid or blended with the structural B mode image. Such an image is commonly referred to as a colorflow display in the case of color-coded velocity, or a power Doppler display in the case of color-coded Doppler signal intensity.

The Doppler processor 30 may employ different processing techniques such as fast Fourier transform (FFT) processing or correlation processing. In a preferred embodiment of the present invention autocorrelation processing is used. An ensemble of samples from each point on a Doppler image line, typically ranging from 2 to 16 samples per ensemble, is stored in an ensemble store 34. An ensemble of fewer samples may be used for display of moving tissue due to the high signal to noise ratio of tissue echoes and the fact that the wall filter is bypassed. The sample data is stored in quadrature I,Q form. An autocorrelator then multiplies adjacent samples in the sequence of samples in complex conjugate form and sums the products to produce a result in the form of I'+jQ'. Mathematically the autocorrelation process can be expressed as $$X' = \sum_{k=1}^{n-1} X_{k+1} \cdot X_k^* \quad (1)$$

where $X_k=I_k+jQ_k$ and n is the number of samples in the sequence. From the complex result the Doppler phase shift $\phi_D$ is calculated by a Doppler detector 38 as the arc tangent of the quotient of Q' and I', or $$\phi_D = \tan^{-1}\frac{Q'}{I'} \quad (2)$$

The Doppler frequency shift $f_D$ is determined by multiplying the phase shift $\phi_D$ by the PRF and dividing by $2\pi$:

$$f_D = \phi_D \frac{PRF}{2\pi} \quad (3)$$

The velocity of the motion is then estimated from the Doppler velocity equation $$v = \frac{f_D c}{2 f_o \cos\theta} \quad (4)$$

by assuming $f_o$ to be the center frequency of the transmitted waveform.

In a preferred embodiment of the present invention two dimensional autocorrelation is used as described in U.S. Pat. No. 5,386,830. The velocities thus determined may be used in a colorflow display by overlaying or blending Doppler color-coded pixels with the B mode image or in a spectral Doppler display of spectral lines. Other Doppler data such as variance, acceleration and power may also be determined from this Doppler data and displayed on the display 50.

When a user desires to view the motion of tissue, such as the motion of the heart walls of the beating heart, the received echo information bypasses the wall filter as symbolically shown by the switch 26, so that the relatively higher amplitude, lower velocity echoes from moving tissue will be processed and displayed. The moving tissue Doppler information is processed by the Doppler processor 30 in the same manner as the bloodflow information. However, since the velocity of moving tissue is generally lower than the velocity of bloodflow, the PRF is usually set to a lower frequency so as to adequately sample the lower frequency motion. The lower PRF setting means that a greater amount of time is required to gather each ensemble of echoes, and hence all of the echoes needed to form a complete image. This necessarily decreases the frame rate of display, the rate at which new images are produced and displayed. A low frame rate of display detracts from the desired performance of the realtime image display.

Figure 2:
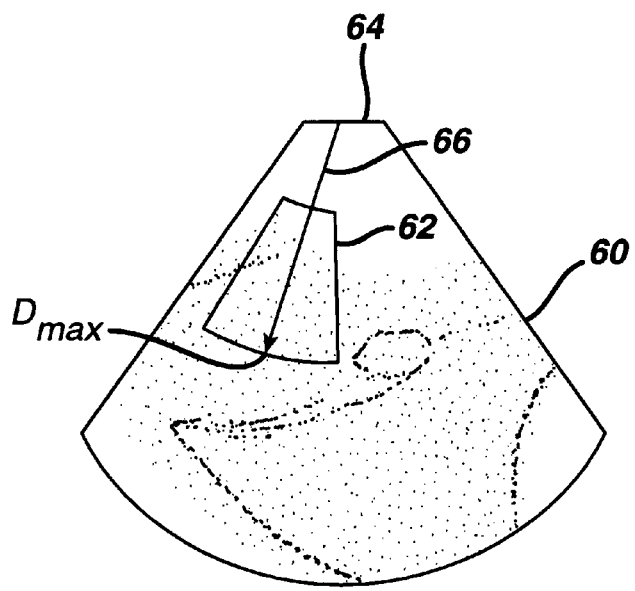
FIG. 2 illustrates an ultrasound image with a color box as produced by an embodiment of the present invention.

In accordance with one aspect of the present invention, a high frame rate of display is maintained by operating the system at a higher PRF than the display PRF chosen by the user, preferably at the maximum possible PRF for the selected maximum depth of the Doppler display. By way of illustration FIG. 2 shows a B mode image 60 of a region of the body being imaged by a probe located at the top 64 of the image. The user has the ability to define a color box 62 within the image in which motion will be detected and displayed. Conventionally the color box 62 may be set to any size and location in the image 60, including occupying the entire image 60. The time required to acquire a line of Doppler echoes from the illustrated box 62 is a function of the maximum depth $D_{max}$ of the box:

$$T = \frac{2D_{max}}{c} \quad (5)$$

where c is the speed of sound in the body. This translates into a pulse repetition interval of $$PRI \geq T = \frac{2D_{max}}{c} \quad (6)$$

and a maximum PRF of $$PRF_{max} = \frac{c}{2D_{max}}$$

When the acquisition PRF is $PRF_a$ and the desired display PRF is $PRF_d$, from equation (2) the phase shift corresponding to the acquisition $PRF_a$ is $$\phi_a = \tan^{-1}\frac{Q'}{I'}$$

The phase shift corresponding to the display $PRF_d$ is obtained by rescaling according to:

$$\phi_d = \phi_a \cdot \frac{PRF_a}{PRF_d} \quad (7)$$

where if $|\phi_d|>\pi$, the value is remapped back to the range $[-\pi,\pi]$. For example when $\phi^d=5\pi/4$, the value is remapped to $\phi_d=-3\pi/4$. Thus, the Doppler frequency corresponding to the display $PRF_d$ is:

$$f_D = \phi_D \frac{PRF_d}{2\pi} \quad (8)$$

Figure 2A:
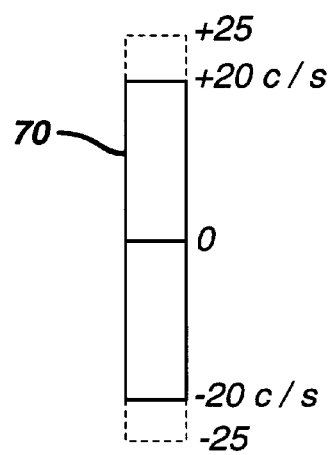
FIG. 2a illustrates a color bar for the ultrasound image of FIG. 2.
Figure 3:
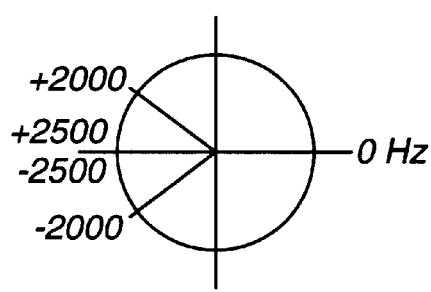
FIGS. 3 and 4 are phase diagrams illustrating the operation of the present invention.

As an example of this aspect of the present invention, suppose that a given depth $D_{max}$ will permit a maximum PRF of 5000 Hz. But suppose that the user desires to see a lower velocity of motion and has set the ultrasound system's PRF to 4000 Hz for display. In this scenario the system of the present invention could acquire Doppler data at the maximum acquisition rate of 5000 Hz, but would rescale the color display to show the 4000 Hz range that the user requested. This is illustrated by the phase diagram of FIG. 3. This phase diagram shows the 0 Hz origin at the right, and frequencies extending to +2500 Hz in the counterclockwise direction and extending to −2500 Hz in the clockwise direction from the origin. This is the range of the PRF used to acquire Doppler ensembles, 5000 Hz. However, the displayed PRF requested by the user in this example is only 4000 Hz, which is indicated by the +2000 Hz and −2000 Hz lines on the phase diagram. To display this requested range over the full length of the color bar 70, shown adjacent to the image 60 in FIG. 2a, the requested range of 4000 Hz is scaled in proportion to its relation to the acquisition range of 5000 Hz. This particular example will use a scale factor of 5000/4000, or 5/4. The range of values from −2000 Hz to +2000 Hz is scaled by this factor to display the desired display PRF over the full color bar 70. This is indicated in FIG. 2a, where the color bar is shown extending between +20 cm/sec and −20 cm/sec (the 4000 Hz range) instead of the acquisition range of +25 cm/sec to −25 cm/sec shown by the dashed extensions to the solid color bar 70.

In the foregoing example, the frame rate of display is improved by 25%, since 5000/4000=125%.

Figure 4:
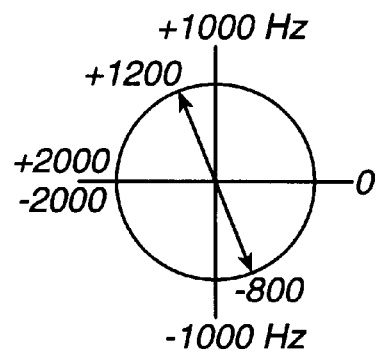

It is always possible that the velocity of the motion being displayed will from time to time momentarily exceed the display range requested by the user, resulting in aliased color values in the Doppler display. Techniques are known for detecting these aliasing conditions and displaying appropriate colors for the conditions. A preferred embodiment of the present invention will similarly display aliasing conditions, which is straightforward since conditions which exceed the requested display PRF range may not exceed the acquisition PRF range. FIG. 4 illustrates such a situation, where the acquisition PRF range extends from −2000 Hz to +2000 Hz, and the user has requested a display range of −1000 Hz to +1000 Hz. In this example the ultrasound system has momentarily detected a velocity of +1200 Hz, which is beyond the upper limit of the requested display range. The user would expect this excessive velocity 25 to alias, and an embodiment of the present invention can produce an aliased result by relocating the +1200 Hz vector for display at its alias location of −800 Hz, resulting in its color display as a −800 Hz value. Thus, the display will alias for the selected display range just as the user expects.

Figure 5:
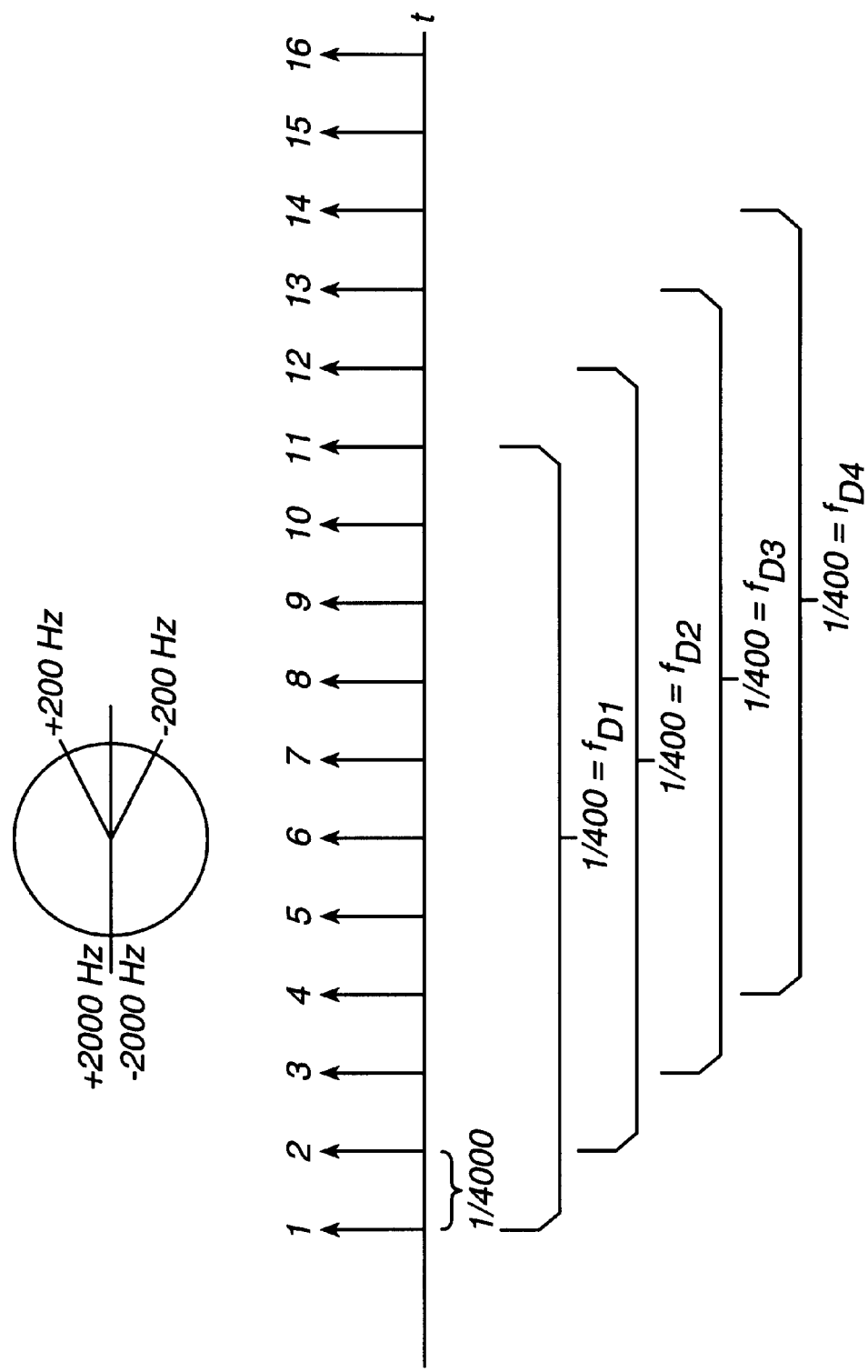
FIG. 5 illustrates Doppler processing in accordance with the principles of the present invention.

An embodiment of the present invention can provide both an improved display rate and improved noise performance of Doppler estimation as compared with conventional techniques. Referring to the illustration of FIG. 5, an autocorrelation implementation of the present invention is depicted. As mentioned above, the conventional autocorrelation technique will operate upon adjacent samples in a sequence of received echoes from a point in the body. In accordance with another aspect of the present invention, autocorrelation is performed using nonadjacent samples of oversampled Doppler data. In FIG. 5 the acquisition PRF is 4000 Hz, ranging from −2000 Hz to +2000 Hz as shown by the phase diagram at the top of the drawing. A PRF of 4000 Hz implies a PRI interval between transmit pulses of 1/4000 Hz, or 0.25 msec, as shown by the arrows representing 16 sampling times at a given location in the body. In this example the user desires to image the motion of slow moving tissue and has called for a display PRF of 400 Hz, ranging from −200 Hz to +200 Hz as shown in the phase diagram. To produce this display PRF samples separated by the desired display PRI of 1/400 Hz are used in the autocorrelation equation to produce a sequence of frequency shift estimates $f_D$, which are summed as called for by the autocorrelation process. Thus, the autocorrelation process can be expressed as $$X' = \sum_{k=1}^{n-PRF_a/PRF_d} X_{k+PRF_a/PRF_d} \cdot X_k^* \qquad (9)$$

where $PRF_a/PRF_d$ is the ratio of the acquisition $PRF_a$ to the display $PRF_d$. As FIG. 5 illustrates, the oversampling accomplished by the high acquisition PRF enables a series of Doppler frequency shift estimates $f_{D1}$, $f_{D2}$, $f_{D3}$ etc. to be calculated in rapid succession. These multiple estimates are summed to produce a more noise-immune estimate as compared to use of samples acquired at the display PRF alone. The rapid succession of calculations means that the frame rate of display can be a function of the higher acquisition PRF rather than the lower display PRF, providing desirably higher realtime frame rates of display.

Both techniques of the present invention can be used simultaneously, if desired. For instance, if the desired display PRF is 400 Hz and the maximum acquisition PRF is 4000 Hz, an ensemble can be acquired at the 4000 Hz rate and autocorrelation performed on the products of sample pairs($X_m$) and ($X_{m+4}$) to produce Doppler phase estimates at 1000 Hz. These estimates can then be rescaled by a factor of 2.5 to yield the desired display range of 400 Hz.

Figure 6:
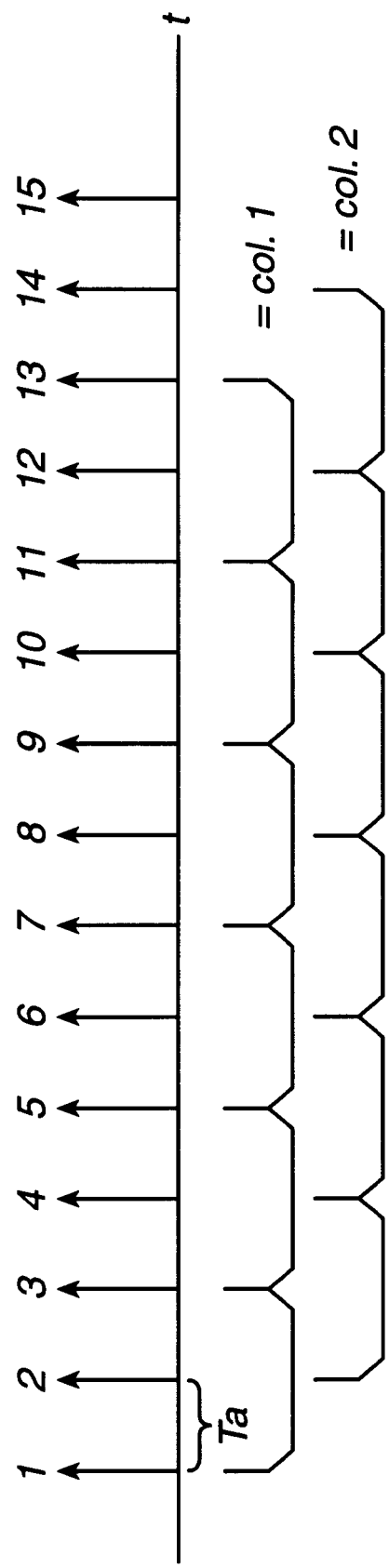
FIG. 6 spectral Doppler processing in accordance with the principles of the present invention.

The principles of the present invention are also applicable to spectral Doppler and color M-mode displays. FIG. 6 illustrates a sequence of samples acquired at intervals of $T_a$ from a given sample volume location. Spectral lines are produced by use of nonadjacent samples as shown below the sample arrows. A first spectral line, col. 1, is formed by Fourier transform processing (in the case of spectral Doppler; autocorrelation is preferred for color M-mode processing) of the first, third, fifth, etc. samples. The next spectral line, col. 2, is formed by Fourier transform processing (or autocorrelation) of the second, fourth, sixth, etc. samples. For each spectral line another successive nonadjacent grouping of samples is used. As demonstrated above in the example of color Doppler, more rapid spectral line display rate results in comparison with conventional processing of adjacent samples.

The present invention can be employed in combination with known techniques for time-multiplexing of the acquisition of Doppler ensembles from a group of lines simultaneously. The acquisition techniques of the present invention can be time-multiplexed, if desired. But one problem which arises when time-multiplexing the ensemble acquisition of a group of lines is that a significant temporal discontinuity develops at the boundary between line groups. Such a problem can be easily avoided with the present invention, since the interval during which a line is rapidly oversampled is relatively short. Thus, little is to be gained by time-multiplexing the acquisition of Doppler data in the practice of the present invention, and time-multiplexing can be disregarded to avoid the temporal discontinuities and the visual banding they produce in the image.

However, time-multiplexed acquisition and the oversampling technique of the present invention can be advantageously combined if desired. For example, suppose that two lines are to be acquired by time-multiplexing, the maximum acquisition PRF (from equation (6)) is 5000 Hz, and the desired display PRF is 2000 Hz. Since, for time-multiplexing, the acquisition PRF must be an integer multiple of the display PRF, conventional time-multiplexed acquisition would employ a multiplexing factor of 2, resulting in:

$PRF_a$=4000 Hz, and $PRF_d$=2000 Hz

But with the use of the present invention, $PRF_a$=5000 Hz, resulting in the sampling of each line by a multiplexing factor of 2 at a $PRF_{line}$=2500 Hz. Doppler estimates would be taken at the 2500 PRF of each sequence using equation (1) then, using equations (7) and (8) (see FIGS. 3 and 4), remapped to the desired 2000 Hz display $PRF_d$. With the higher acquisition $PRF_a$ of 5000 Hz, there will be a 25% improvement in the display frame rate over time-multiplexing alone.

What is claimed is:

1. A method for operating an ultrasonic diagnostic imaging system to image the motion of substances inside the body by Doppler techniques, including an ultrasonic probe which is operable by a user to transmit ultrasonic waves at a pulse rate frequency (PRF) and to receive Doppler signals from a point in the body in response to said transmitted waves, a Doppler processor which processes said Doppler signals for display within a range of Doppler values, and a display which displays Doppler values within said range comprising the steps of:

controlling said system to acquire Doppler information down to a given depth from said probe;

controlling said system to display a desired range of Doppler values which corresponds to a given PRF rate;

controlling said probe to transmit ultrasonic waves at a rate which is greater than said given PRF rate but not greater than the maximum PRF for said given depth; and processing received Doppler signals for display of Doppler values within said desired range.

2. The method of claim 1, wherein said step of controlling said probe comprises operating said probe to transmit at the maximum PRF for the speed of sound in said body at said given depth.

3. The method of claim 1, wherein said received Doppler signals correspond to a given range of Doppler values which is greater than said desired range.

4. The method of claim 3, wherein said step of processing comprises scaling Doppler signals within said given range to correspond to said desired range.

5. The method of claim 4, wherein said given range corresponds to a given range of velocity values and wherein said desired range corresponds to a range of velocity values which is less than said given range.

6. The method of claim 4, wherein said given range corresponds to the PRF at which said Doppler signals were acquired from the body, and wherein said desired range corresponds to a PRF which is less than said acquisition PRF.

7. The method of claim 1, wherein said processing step comprises processing Doppler signals which are outside said given range and within the range defined by said transmit PRF to be displayed as aliased Doppler values of said given range.

8. A method for operating an ultrasonic diagnostic imaging system to image the motion of substances inside the body by Doppler techniques, including an ultrasonic probe which is operable by a user to transmit ultrasonic waves at a pulse rate frequency (PRF) and to receive Doppler signals from a point in the body in response to said transmitted waves which sample the effects of motion at said point, a Doppler processor which processes said Doppler signals for display of motion within a range of Doppler values, and a display which displays motion within said range comprising the steps of:

controlling said system to display a desired range of motion which corresponds to a given sampling rate;

controlling said probe to transmit ultrasonic waves at a rate which oversamples said motion in relation to said given sampling rate; and processing Doppler signals received in response to said oversampling for display within said desired range of motion.

9. The method of claim 8, wherein said given sampling rate corresponds to a display PRF, and wherein said probe is controlled to transmit ultrasonic waves at a PRF which is greater than said display PRF.

10. The method of claim 8, wherein said step of processing comprises scaling oversampled motion values for display within said desired range of motion.

11. The method of claim 10, wherein said oversampled motion values correspond to a given range of velocity values and wherein said desired range of motion corresponds to a range of velocity values which is less than said given range.

12. The method of claim 9, wherein said desired range of motion corresponds to a PRF which is less than said transmit PRF.

13. The method of claim 8, wherein said processing step comprises processing motion which is outside said desired range and within the range of motion defined by said oversampling to be displayed as aliased motion of said desired range.

14. An ultrasonic diagnostic imaging system for imaging the motion of substances inside the body by Doppler techniques, comprising:

an ultrasonic probe which is operable by a user to transmit ultrasonic waves at a pulse rate frequency (PRF) and to receive Doppler signals from a point in the body at an acquisition PRF in response to said transmitted waves;

a Doppler processor which processes said Doppler signals for display within a range of Doppler values corresponding to a display PRF which is less than said acquisition PRF; and a display which displays Doppler values within said range.

15. The ultrasonic diagnostic imaging system of claim 14, wherein said Doppler processor further comprises a scaling circuit for scaling Doppler values in correspondence to said range of Doppler values.

16. The ultrasonic diagnostic imaging system of claim 14, wherein said probe receives said Doppler signals from a point in the body in a sequence; and wherein said Doppler processor further comprises an autocorrelator which performs autocorrelation on said sequence by operating upon nonadjacent signals in said sequence.

17. The ultrasonic diagnostic imaging system of claim 14, wherein said Doppler processor further comprises an aliasing circuit for displaying within said range Doppler values which are outside said range and within a range of values delineated by said acquisition PRF.

\* \* \* \* \*